United States Patent [19]

Peterson

[11] 4,231,785
[45] Nov. 4, 1980

[54] HERBICIDE ANTIDOTES

[75] Inventor: Larry W. Peterson, Oakdale, Calif.

[73] Assignee: Shell Oil Company, Houston, Tex.

[21] Appl. No.: 41,266

[22] Filed: May 21, 1979

Related U.S. Application Data

[63] Continuation-in-part of Ser. No. 937,621, Aug. 28, 1978, abandoned.

[51] Int. Cl.$^3$ .................. A01N 25/32; A01N 43/70; A01N 43/36
[52] U.S. Cl. ............................................. 71/93; 71/95
[58] Field of Search ............................... 71/93, 95

[56] References Cited

U.S. PATENT DOCUMENTS 3,620,710  11/1971  Schwarze .......................... 71/93

Primary Examiner—Catherine L. Mills

[57] ABSTRACT

The safety of the herbicide, cyanazine, with respect to grain sorghum, is improved by use of a selective antidote, which is a compound of the formula:

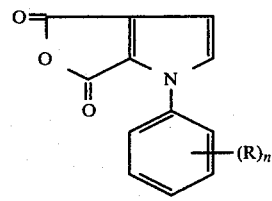

wherein the symbols have defined meanings.

5 Claims, No Drawings

HERBICIDE ANTIDOTES

This application is a continuation-in-part of application Ser. No. 937,621, filed on Aug. 28, 1978, abandoned.

BACKGROUND OF THE INVENTION

Cyanazine (2-chloro-4-(ethylamino)-6-(1-cyano-1-methylethylamino)-1,3,5-triazine) is used commercially as a herbicide. It is not generally satisfactory for controlling weeds in plantings of grain sorghum, since it tends to be rather toxic with respect to the sorghum plants at the dosages required to control the weeds.

DESCRIPTION OF THE INVENTION

It has been found that the phytotoxicity of the herbicide, cyanazine, with respect to grain sorghum plants, can be decreased without significant reduction in its effectiveness with respect to controlling weeds, by use of an antidote, which is a compound of the formula:

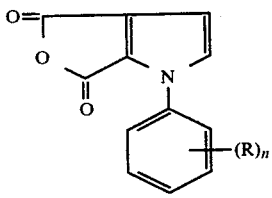

wherein n and R are as follows:

| Compound No. | n | R* |
|---|---|---|
| 1 | 0 | — |
| 2 | 1 | 3-(—Cl) |
| 3 | 1 | 2-(—F) |
| 4 | 1 | 3-(—CF$_3$) |
| 5 | 1 | 2-(—Cl) |
| 6 | 2 | 2-(—Cl),5-(—Cl) |

*The number indicates the position of the substituent(s) on the indicated phenyl)

At the antidotally effective dosages, these antidotes are not phytotoxic to the sorghum plants.

Cyanazine can be applied pre-emergence, or post-emergence, being taken up by the roots and foliage of the plants that it contacts.

Depending upon the way(s) the antidote and herbicide are applied, the antidote is applied at, or before, the time the herbicide is applied, the essential requirement being that the antidote be present in the sorghum plant a sufficient time before the herbicide contacts the plant to provide the antidotal effect. Thus, the antidote can be applied to the sorghum seeds, and the herbicide applied at the time the seeds are planted, or afterwards, either before or after the sorghum plant's foliage has emerged from the soil. Also, since the antidote passes through the soil more rapidly than does the herbicide, the antidote can be applied to the soil in which the sorghum seeds are to be planted at, or before, or after, the time the sorghum seeds are planted therein and before the sorghum plant's foliage has emerged from the soil and the herbicide applied at the time the seeds are planted, or afterwards, either before or after the sorghum plant's foliage has emerged from the soil. Further, both the antidote and the herbicide can be applied after the sorghum plant's foliage has emerged from the soil. However, in this case, the herbicide is absorbed very rapidly by the sorghum plant, so that the antidote must be applied at least one day, and preferably two to three days before the herbicide is applied, to permit the antidote to provide the antidotal effect before the herbicide is applied. To avoid this sequential application of the antidote and the herbicide, and to minimize any possibility of toxicity of the antidote to the sorghum plants, such post-emergent treatment is less attractive than pre-emergence treatment.

To summarize, as a general matter, to provide the antidotal effect, the antidote must be available to the growing sorghum plant just before the plant is contacted with the herbicide. The available evidence appears to show that the antidote is most effective when in the soil environment of the sorghum plants prior to the time the sorghum seeds have sprouted, whether the herbicide is applied before or after the foliage of the sorghum plant has emerged from the soil. When applied to the soil, the antidote can be placed on the surface of the soil and incorporated into the soil by water (by rain or irrigation techniques) or it can be incorporated in the soil by mixing techniques.

The amount of the antidote that is required will depend upon the way in which it is applied. When applied to the sorghum seeds, the suitable dosage of the antidote is from about 0.25 to about 5, and usually from about 0.5 to about 3, percent of the weight of the seed. When applied to the soil, the suitable dosage of the antidote is from about 0.5 to about 5, usually about 1 to about 4, pounds per acre when applied pre-emergence, and from about 0.25 to about 2, usually about 0.5 to about 1.5, pounds per acre, when applied post-emergence. Since the antidote does not significantly reduce the effectiveness of the herbicide with respect to the weeds to be controlled, the herbicide can be used at the dosages ordinarily recommended.

Whereas the antidote can be used neat, it is ordinarily desirable from the standpoint of effectiveness of application to employ it in the form of a formulation containing in addition to the antidote, one or more materials which enable the antidote to be used most efficiently in a given technique for its application.

Thus, when the antidote is to be coated on sorghum seed, it usually will be found to be desirable to dissolve it in a suitable nonphytotoxic solvent and treat the seeds with the solution, or to mix it with a suitable liquid or solid carrier for treatment of the seed. An adhesive or sticker, such as methyl cellulose, may aid in the formation of a stable coating. Such techniques, as well as techniques for physically effecting the coating, are well known in the art, and may be used to apply antidotes of this invention to sorghum seeds.

For application of the antidotes to soil and/or the foliage of the sorghum plants, the antidotes can be formulated using any of the adjuvants conventionally used in the art, and applied by conventional techniques.

The term "adjuvant" as used herein means a material, which may be inorganic or organic and of synthetic or natural origin, with which the antidote is mixed or formulated to facilitate its application to the plant, seed or soil, or its storage, transport and/or handling. The adjuvant may be a solid or a liquid.

Suitable solid adjuvants are the non-phytotoxic solid carriers conventionally used for application of agricultural chemicals.

Suitable liquid adjuvants include non-phytotoxic solvents for antidotes and non-phytotoxic liquids in which the antidote is insoluble or only slightly soluble.

The formulation suitably can contain one or more surface-active agents. The surface-active agent may be an emulsifying agent or a dispersing agent or a wetting agent. It may be nonionic or ionic. Surface-active agents usually applied in formulating agricultural chemicals are suitable.

The antidotes may be formulated as a wettable powder, as a dust, as granules, solution, emulsifiable concentrate, emulsion, suspension concentrate or aerosol, as convenient for the intended application. Encapsulated formulations and controlled release formulations also are contemplated.

The formulation suitably can also contain other materials, such as dispersing agents, suspending agents such as protective colloids, and thixotropic agents, defoamers, corrosion inhibitors, stabilizers, penetrants and stickers. Certain organic additives or inorganic salts may be dissolved in the carrier to assist in preventing sedimentation or as antifreeze agents.

Aqueous dispersions and emulsions, for example, compositions obtained by diluting a wettable powder or an emulsifiable concentrate with water, are suitable.

The formulations of the antidote may also contain other ingredients, for example, other compounds possessing insecticidal, nematodal, fungicidal and/or bactericidal properties.

As a class, the antidotes are known compounds. Thus, Compound 1 is disclosed in Huisgen and Laschtuvka, Chemische Berichte, 93, 65–81 (1960), and was prepared by the method shown therein. The other antidotes were prepared by treating the appropriate dicarboxylic acid,

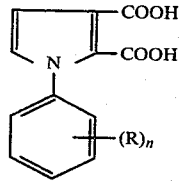

with an excess of acetic anhydride at reflux for about two hours, then evaporating the unreacted acetic anhydride under reduced pressure, and recrystallizing the residue to give the desired product. In this manner were obtained Compounds 2 (m.p.: 175°–176° C.), 3 (m.p.: 150°–151° C.), 4 (m.p.: 132°–134° C.), 5 (m.p.: 140°–143° C.), and 6 (m.p.: 178°–180° C.). In all cases, the identities of the products and of the uncommon starting materials and intermediates were confirmed by appropriate chemical and spectral analyses.

Other dicarboxylic acid precursors were prepared as follows:

1-(3-chlorophenyl)-1H-pyrrole-2,3-dicarboxylic acid (I)

A mixture of 9.2 g of the diethyl ester of 3,6-dicyano-2,7-dihydroxy-2,4,6-octatrienedioic acid (Huisgen and Laschtuvka, supra), 7.0 g of 3-chloroaniline and 75 ml of dry toluene was stirred at reflux for 3 hours, water of reaction being distilled from the mixture as it was formed. The resulting mixture was filtered and the solvent was evaporated under reduced pressure. The residue was dissolved in 35 ml of hot ethanol and the solution was chilled in a freezer. The resulting solid was filtered and dried under vacuum to give the ethyl ester of 3-cyano-1-(3-chlorophenyl)-1H-pyrrole-2-carboxylic acid (IA), m.p.: 113°–116° C.

5.1 g of IA in 10 ml of ethanol was mixed with 3.0 g of sodium hydroxide in 30 ml of water and the mixture was stirred and refluxed for 66 hours. The mixture was cooled, and acidified with 20 ml of 6 N hydrochloric acid. The solid was filtered, and rinsed with water. It was dissolved in acetone, the solution was filtered, the filtrate was concentrated and mixed with water, and the mixture was placed in a freezer. The solid was filtered and vacuum dried, to give I, m.p.: 214°–215° C. (with decomposition).

The other precursor dicarboxylic acids were prepared in a similar manner: R=2-fluoro (m.p.: 215°–217° C. (with decomposition)), R=3-Trifluoromethyl (m.p.: 198°–199° C. (with decomposition)), R=2-chloro (m.p.: 210°–212° C. (with decomposition)), R=2,5-dichloro (m.p.: 105°–110° C. (with decomposition)).

The usefulness of these compounds to ameliorate the effect of cyanazine with respect to grain sorghum was established as follows:

EXAMPLE 1

Grain sorghum seeds (Pioneer 828) were planted in 4-inch pots, in sand, and were watered with one-quarter strength Hoagland's solution (D. R. Hoagland and D. I. Arnon, The Water Culture Method for Growing Plants Without Soil, Circular 347, University of California). After one week of growth under continuous light, the seedlings were watered for two days with the Hoagland's solution containing the test compound at (a) 3 and (b) 0.3 micrograms per milliliter. On the following two days, the plants were watered with Hoagland's solution containing BLADEX ® Herbicide (containing approximately 80% by weight of cyanazine) to provide 0.5 or 1.5 micrograms of cyanazine per milliliter of solution. The higher dosage of cyanazine was deliberately chosen for causing complete death of the sorghum plants, with the lower dosage being sufficient to cause severe damage to the plants. Two weeks later, the plants were visually checked and the damage rated on a scale of zero to nine, zero indicating no observable effect and nine indicating complete death of the plants. The results are set forth in Table I.

TABLE I

| Dosage of Test Compound (μg/ml) | 3.0 | 0.3 | 0 | 3.0 | 0.3 | 0 |
|---|---|---|---|---|---|---|
| Dosage of Cyanazine (μg/ml) | 1.5 | 1.5 | 1.5 | 0.5 | 0.5 | 0.5 |
| Compound No. | | | | | | |
| 1 | 5 | 7 | 8 | 1 | 2 | 6 |
| 2 | 9 | 9 | 9 | 5 | 4 | 7 |
| 3 | 8 | 9 | 9 | 2 | 3 | 7 |
|   | 8 | 9 | 9 | 5 | 6 | 7 |
| 4 | 7 | 7 | 9 | 2 | 3 | 6 |
|   | 8 | 8 | 9 | 1 | 2 | 6 |
| 5 | 7 | 8 | 9 | 2 | 3 | 6 |
|   | 8 | 7 | 9 | 1 | 6 | 6 |
| 6 | 8 | 8 | 9 | 3 | 3 | 7 |

In this test, a recording of 7 or is 8 is considered to be an indication of a safening effect, compared to a reading of 9.

EXAMPLE 2

Grain sorghum seeds (Pioneer 828) were planted in sandy loam soil in pots. One series of pots was treated with Compound 1 only, one series with BLADEX Herbicide only and one series with both. The herbicide was formulated as a wettable powder, containing approximately 80% by weight of cyanazine. Compound 1 was applied as a solution in a non-phytotoxic standard solvent, to provide a dosage of Compound 1 of 3 pounds/acre. The plants were watered and held under identical conditions. When the plants were at the second true leaf stage, the herbicide was applied, as a solution in the standard solvent with a sprayer that varied the dosage logarithmically from 0.5 to 5 pounds of cyanazine/acre, over the series of pots that were sprayed. The plants then were watered and all of the pots held under identical conditions. After 14–21 days the condition of the plants was observed, and the dosage (pounds/acre) that would kill 90% of the plants was determined, this being designated as the $GI_{90}$ dosage. The results of the test are summarized in Table II.

TABLE II

| | Treated $GI_{90}$ Dosage | | |
|---|---|---|---|
| Check (No Treatment) | Compound 1 Only | Herbicide Only | Compound 1 + Herbicide |
| Plants normal | Plants normal | 0.5 | 2.5 |

EXAMPLE 3

Grain sorghum seeds (Pioneer 828) were planted in sandy loam soil in pots. Some of the pots were sprayed pre-emergence with a solution of Compound 1 in the standard solvent, to provide a dosage of Compound 1 of 3 pounds/acre. To different series of pots, three formulations of BLADEX Herbicide were then applied: (a) solution in the standard solvent, (b) spray formulation prepared by diluting a wettable powder (WP) concentrate, (c) spray formulation prepared by diluting a water dispersible suspension (WDS) concentrate with water. The formulations were applied with the logarithmic sprayer to provide dosages of cyanazine of from 0.5 to 5 pounds/acre, over the series of pots that were sprayed. In one series, the herbicide was applied pre-emergence, and in another series it was applied post-emergence, the sorghum plants being in the second true leaf stage. When the post-emergence applications were made, the herbicide was deposited on the soil surface, as well as the leaves. To separate the activity of the herbicide on the soil from that on the foliage, a test series was conducted in which the soil in the pots was covered with vermiculite, and after spraying, the vermiculite was removed with a vacuum cleaner, leaving the surface of the soil free of herbicide.

All of the pots then were watered and treated identically until observations were made 21 days later. From the data thus obtained was determined the dosages (pounds/acre) that caused 10% and 90% kill of the plants, respectively, these being designated as the $GI_{10}$ and $GI_{90}$ dosages, respectively. The results of the pre-emergence applications are summarized in Table III, the results of the post-emergence tests being summarized in Table IV.

TABLE III

| Herbicide Formulation | Compound 1 | Sorghum $GI_{10}$ | Sorghum $GI_{90}$ |
|---|---|---|---|
| Technical | $-^a$ | $0.5^b$ | 0.5 |
| | + | 1.0 | 2.5 |
| WDS | − | 0.5 | 0.5 |
| | + | 1.0 | 2.3 |
| WP | − | 0.5 | 0.9 |
| | + | 1.0 | 2.5 |

$^a$ − indicates absent + indicates present
$^b$ units are in pounds per acre

TABLE IV

| Herbicide Formulation | Compound 1 | Vermiculite on Surface | Sorghum $GI_{10}$ | Sorghum $GI_{90}$ |
|---|---|---|---|---|
| Technical | $-^a$ | $-^a$ | $0.5^b$ | 0.5 |
| | + | − | 0.5 | 1.0 |
| | − | + | 0.5 | 1.3 |
| | + | + | 1.0 | 1.6 |
| 4 WDS | − | − | 0.5 | 1.5 |
| | + | − | 1.5 | 2.0 |
| | − | + | 2.3 | 3.0 |
| | + | + | 4.0 | 5.0 |
| 4 WDL | − | − | 0.6 | 1.0 |
| | + | − | 1.7 | 2.5 |
| | − | + | 1.3 | 2.3 |
| | + | + | 5.0 | 5.0 |
| 80 WP | − | − | 0.5 | 1.0 |
| | + | − | 2.5 | 3.0 |
| | − | + | 1.5 | 2.8 |
| | + | + | 4.0 | 5.0 |

$^a$ − indicates absent
+ indicates present
$^b$ units are in pounds per acre

EXAMPLE 4

Various weed seeds were planted in sandy loam soil in pots. One series of pots was treated with Compound 1; a second series was treated with Compound 1, then with cyanazine; a third series was treated with cyanazine only, and a fourth series was left as an untreated check. Compound 1 was applied uniformly at 3 pounds per acre while cyanazine was applied at dosages that varied logarithmically from 0.5 to 5 pounds per acre over the pots. After $2\frac{1}{2}$ weeks under identical growing conditions, all of the plants were observed, and the dosage (pounds per acre) that would kill 90% of the plants was determined. The results of the test are summarized in Table V.

TABLE V

| | $GI_{90}$ Dosage (lbs/A) | | | |
|---|---|---|---|---|
| Weed Species | Cyanazine | Cyanazine + Compound 1 | Compound 1 | Check |
| Johnson Grass | 3.7 | 1.7 | $-^a$ | − |
| Crab Grass | <0.5 | 1.7 | − | − |
| Water Grass | 0.7 | 1.2 | − | − |
| Downy Brome | <0.5 | <0.5 | − | − |
| Morning Glory | <0.5 | <0.5 | − | − |
| Pigweed (Red Root) | <0.5 | <0.5 | − | − |
| Sickle Pod | <0.5 | <0.5 | − | − |
| Mustard | <0.5 | <0.5 | − | − |

$^a$ − indicates that no effect was observed.

EXAMPLE 5

A series of tests were conducted by the procedures described in Example 2, the herbicide being applied pre-emergence, and Compound 1 being applied pre-emergence in some cases, and applied to the seed in other cases. The compound was applied to the seed by spraying an acetone solution of the compound, also containing a sticker, onto the agitated seed under conditions that effected rapid evaporation and removal of the solvent. The seed was coated by approximately three percent of its weight of Compound 1. The results were reported as the $GI_{10}$ and $GI_{90}$ dosages in pounds/acre and are reported in Table VI.

TABLE VI

| Type of Herbicide Application | Safener | Type of Application | $GI_{10}$ | $GI_{90}$ |
|---|---|---|---|---|
| Pre[a] | —[b] | — | 0.5 | 1.0[c] |
| | — | — | <0.5 | 0.7 |
| | — | — | 0.7 | 1.0 |
| | + | Pre | 1.0 | 1.7 |
| | + | Seed | 1.2 | 2.1 |
| Post[a] | — | — | <0.5 | <0.5 |
| | — | — | <0.5 | 0.9 |
| | + | Seed | 0.8 | 1.8 |
| | + | Pre | 1.5 | 3.4 |
| | + | Pre | 1.5 | 3.0 |

[a]Pre — indicates pre-emergence application Post — indicates post-emergence application
[b]— indicates absent + indicates present
[c]pounds per acre

EXAMPLE 6

Compound 1 was tested in the field using Pioneer 828 Sorghum seed as follows: Compound 1 was applied at a dosage of 3 pounds/acre, in sandy loam soil, by four techniques: (1) pre-planting incorporation by mixing (PPI); (2) pre-emergence spray on the soil (PE); (3) postemergence spray (PO); (4) coated in the seed (seed) (3% by weight). BLADEX Herbicide (formulated as in Example 2) was applied (1) PPI, (2) PE and (3) PO, by a logarithmic sprayer which provided a dosage varying from a low dosage of cyanazine/acre at one end of the test plot to a high dosage at the other end. In all cases, the plots were irrigated by sprinklers shortly after application of the chemicals. Spray formulations of the herbicide were prepared by diluting either a wettable powder concentrate (WP) or a water dispersible liquid concentrate (WDL). The results were evaluated about three weeks after this treatment, and are reported in Table VII, as the $GI_{70}$ and $GI_{90}$ dosages (pounds/acre).

The test plots were also over seeded with certain weed species to see if Compound 1 might moderate cyanazine activity with respect to weeds. As can be seen from Table VIII compound 1 did not adversely affect the herbicidal activity of cyanazine with respect to any of the weeds.

TABLE VII

| | Test 1 | | Test 2 | |
|---|---|---|---|---|
| Treatment | $GI_{70}$ | $GI_{90}$ | $GI_{70}$ | $GI_{90}$ |
| Herbicide - PE | <0.2 | <0.2 | <0.2 | 0.3 |
| + Compound 1 - Seed | 0.3 | 0.9 | 0.5 | 0.6 |
| Herbicide WP - PO | 0.5 | 0.6 | 0.5 | 1.1 |
| + Compound 1 - Seed | 1.4 | 1.8 | 1.1 | 3.0 |
| Herbicide WDL - PO | 0.5 | 0.5 | 0.4 | 0.6 |
| + Compound 1 - Seed | 1.2 | 1.6 | 1.1 | 1.7 |
| Herbicide - PE | 0.3 | 0.4 | 0.4 | 0.5 |
| + Compound 1 - PE | 0.6 | 1.5 | 0.7 | 1.5 |
| + Compound 1 - PPI | 0.3 | 0.5 | 0.5 | 0.6 |
| Herbicide WP - PO | 2.3 | 2.9 | 1.8 | 2.7 |
| + Compound 1 - PE | 2.1 | 3.2 | 1.5 | 3.0 |
| + Compound 1 - PO | >5.0 | >5.0 | 3.8 | 4.1 |
| Herbicide WDL - PO | 1.3 | 2.3 | 2.7 | 3.1 |
| + Compound 1 - PE | 1.8 | 3.1 | 2.0 | 2.6 |
| + Compound 1 - PO | 3.0 | >5.0 | 2.1 | 3.1 |

TABLE VIII

| | $GI_{90}$ Ratings | | | | | |
|---|---|---|---|---|---|---|
| Treatment | Crab Grass | Annual Ryegrass | Mustard | Red Root Pigweed | Prostrate Pigweed | Lambs Quartere |
| Bladex WP PE | 0.1 | 0.1 | 0.3 | 0.4 | 0.7 | <0.1 |
| + Compound 1 PE | <0.1 | <0.1 | 0.1 | 0.4 | 1.3 | <0.1 |
| + Compound 1 PPI | <0.1 | <0.1 | <0.1 | 0.15 | 0.25 | <0.1 |
| Bladex WP PO | <0.4 | <0.4 | <0.4 | 0.8 | 0.8 | <0.4 |
| + Compound 1 PE | <0.4 | <0.4 | <0.4 | <0.4 | 0.4 | <0.4 |
| + Compound 1 PO | 0.5 | 0.6 | <0.4 | 1.0 | 1.0 | 0.5 |
| Bladex WDL PO | <0.4 | <0.4 | <0.4 | <0.4 | <0.4 | <0.4 |
| + Compound 1 PE | <0.4 | <0.4 | <0.4 | <0.4 | <0.4 | <0.4 |
| + Compound 1 PO | 0.9 | 0.8 | <0.4 | <0.4 | <0.4 | <0.4 |

It has been found that the effectiveness of the antidotes of this invention appears to differ from variety to variety of grain sorghum: with respect to most varieties, it appears that the antidote significantly reduces the toxicity of cyanazine, but in some cases it appears to have no significant effect. It has been noted that with respect to many varieties of grain sorghum, application of one of the antidotes of the invention results in the formation of red spots on the foliage of the plants, which are believed to result from the formation of anthocyanins. It has been further noted that in general, the antidotes appear to be effective with respect to those varieties of sorghum which become spotted when the antidote is applied to the plant, and appear to be ineffective with respect to those varieties of sorghum which do not become spotted when the antidote is applied. However, about 10–15% of the varieties tested do not follow this pattern, i.e., some varieties form the spots, but the antidote is not effective; some do not from the spots, but the antidote is effective. At the present time, the applicant does not have an explanation for these phenomena. However, with respect to any particular variety of grain sorghum other than those of Example 7, infra, it is a simple matter to ascertain whether an antidote is effective by testing the variety according to the procedure described in Example 1, supra.

EXAMPLE 7

A number of varieties of grain sorghum were tested according to the procedure described in Example 1. Each variety was observed and rated for two effects: extent of spotting and effectiveness of the antidote. The extent of spotting was rated on a zero-to-five scale, zero indicating no spotting, and five indicating heavy spotting, with a rating of two or less being considered to be insufficient to be significant. Effectiveness of the antidote was rated as in index.

Effectiveness Index =

$$\left(\begin{array}{c}\text{damage rating,}\\ \text{cyanazine alone}\end{array}\right) \text{minus} \left(\begin{array}{c}\text{damage rating,}\\ \text{cyanazine + antidote}\end{array}\right)$$

An antidote was considered to be effective if the index was 3 or above. The damage ratings were determined as described in Example 1. The dosage of cyanazine (0.5 micrograms/milliliter) was chosen to give a damage rating of cyanazine alone of about seven. The dosage of antidote (Compound 1 in all cases) was 3.0 micrograms/milliliter.

The results are set out in Table IX.

TABLE IX

| Variety of Sorghum | Spotting Rating | Effectiveness Index |
|---|---|---|
| SERIES A[a] | | |
| Pioneer | | |
| P-8199 | 3 | 4 |
| P-8283 | 4 | 4 |
| P-8225 | 3 | 4 |
| P-828 | 4 | 5 |
| P-8272 | 4 | 3 |
| P-8311 | 5 | 4 |
| P-8324 | 3 | 6 |
| P-8442 | 3 | 6 |
| P-8475 | 4 | 5 |
| P-8501 | 3 | 4 |
| P-8585 | 3 | 5 |
| P-8592 | 3 | 3 |
| P-8626 | 4 | 3 |
| P-8633 | 3 | 4 |
| P-B877 | 3 | 5 |
| P-8790 | 4 | 4 |
| P-883 | 3 | 4 |
| P-894 | 3 | 3 |
| P-944 | 3 | 5 |
| P-931 | 5 | 3 |
| Funk | | |
| G-251 | 4 | 5 |
| G-499GBR | 3 | 8 |
| G-623GBR | 3 | 3 |
| DeKalb | | |
| A-28+ | 4 | 6 |
| B-35 | 4 | 5 |
| C-42a+ | 4 | 6 |
| E-57+ | 3 | 4 |
| D-55 | 5 | 3 |
| F-67 | 4 | 5 |
| F-68 | 5 | 6 |
| FS-25a+ | 3 | 5 |
| Ferry Morse | | |
| Amak R-10 | 3 | 5 |
| Amak R-12 | 3 | 5 |
| Advance 10-53 | 3 | 4 |
| Advance 19-22 | 4 | 6 |
| Advance 14 | 4 | 5 |
| Advance 83GR | 3 | 4 |
| Advance 80 | 3 | 4 |
| Advance 82 | 3 | 3 |
| Advance 53A | 5 | 6 |
| Advance 7702 | 3 | 7 |
| Northrup King | | |
| NK 265 | 3 | 5 |
| NK 2650 | 4 | 3 |
| Breeding Parents | | |
| Purple CK60B | 3 | 3 |
| KS-53 | 5 | 3 |
| RB-60R | 3 | 3 |
| TX-414R | 3 | 3 |
| N 9040R | 3 | 3 |
| Wheat A | 5 | 4 |
| Wheat B | 5 | 4 |
| CK 60A | 3 | 4 |
| CK 60B | 3 | 4 |
| SERIES B[a] | | |
| Pioneer | | |
| P-B815 | 2 | 0 |
| P-8308B | 2 | 1 |
| P-8386 | 1 | 1 |
| P-8417 | 1 | 1 |
| P-8442 | 2 | 0 |
| P-8451 | 1 | 0 |
| P-8454 | 2 | 0 |
| P-8674 | 1 | 0 |
| P-8712 | 2 | 2 |
| P-923 | 2 | 2 |
| DeKalb | | |
| D-46 | 1 | 1 |
| BR-64 | 2 | 1 |
| Northrup King | | |
| NK 2233 | 2 | 0 |
| NK 2778 | 2 | 2 |
| Breeding Parents | | |
| Leoti Red | 0 | 0 |
| Tan Ck Atlas | 2 | 1 |
| Purple Ck Atlas | 0 | 0 |
| Tan Texicoa | 0 | 0 |
| Atlas Green | 0 | 0 |
| Early Hegari | 2 | 2 |
| Rox Green | 0 | 0 |
| Red Tan H | 1 | 0 |
| Red Tan B | 1 | 0 |
| SERIES C[a] | | |
| Pioneer | | |
| P-8155 | 3 | 2 |
| P-820 | 4 | 2 |
| Funk | | |
| G-522DR | 3 | 1 |
| G-522A | 3 | 0 |
| Northrup King | | |
| NK-129 | 4 | 0 |
| SERIES D[a] | | |
| Pioneer | | |
| P-866 | 1 | 4 |
| P-956 | 1 | 5 |
| P-947 | 2 | 6 |
| DeKalb | | |
| DD-50 | 2 | 4 |
| B-39y+ | 1 | 4 |
| C-43y+ | 1 | 4 |
| Northrup King | | |
| NK-1580 | 1 | 6 |

[a] Series A: varieties which spot; antidote is effective;
Series B: varieties which do not spot; antidote is not effective;
Series C: varieties which spot; antidote not effective;
Series D: varieties which do not spot; antidote is effective.

I claim:

1. A method for increasing the safety of the herbicide, cyanazine, with respect to a grain sorghum plant, which comprises making available to the growing sorghum plant, just before the plant is contacted with the herbicide, an effective amount of one of six antidote compounds of the formula:

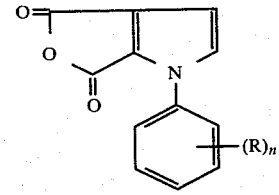

wherein in each of said compounds, n and R are as follows:

| n | R |
|---|---|
| 0 | — |
| 1 | 3-(—Cl) |
| 1 | 2-(—F) |
| 1 | 3-(—CF$_3$) |
| 1 | 2-(—Cl) |
| 2 | 2-(—Cl),5-(—Cl) | wherein the number indicates the position of the substituent, R, on the indicated phenyl ring.

2. A method according to claim 1 wherein the antidote compound is applied to the grain sorghum seed before it is planted.

3. The seed produced by the method of claim 2.

4. A method according to claim 1 wherein the antidote compound is introduced into the soil before or at the time the sorghum seed is planted therein.

5. A method according to claim 1 wherein the antidote compound is introduced into the soil wherein the sorghum plant is growing.

* * * * *